US010324010B2

(12) United States Patent
Freeman

(10) Patent No.: US 10,324,010 B2
(45) Date of Patent: Jun. 18, 2019

(54) POWDER OR GRANULATED MATERIAL TEST APPARATUS

(71) Applicant: FREEMAN TECHNOLOGY LIMITED, Tewkesbury, Gloucestershire (GB)

(72) Inventor: Timothy Freeman, Tewkesbury (GB)

(73) Assignee: FREEMAN TECHNOLOGY LIMITED, Tewkesbury, Gloucestershi (GB)

(*) Notice: Subject to any disclaimer, the term of this patent is extended or adjusted under 35 U.S.C. 154(b) by 12 days.

(21) Appl. No.: 15/573,004

(22) PCT Filed: May 10, 2016

(86) PCT No.: PCT/GB2016/051332
§ 371 (c)(1),
(2) Date: Nov. 9, 2017

(87) PCT Pub. No.: WO2016/181125
PCT Pub. Date: Nov. 17, 2016

(65) Prior Publication Data
US 2018/0149560 A1 May 31, 2018

(30) Foreign Application Priority Data
May 12, 2015 (GB) .................................. 1508054.2

(51) Int. Cl.
*G01N 1/28* (2006.01)
*G01N 11/14* (2006.01)

(52) U.S. Cl.
CPC ............ *G01N 1/286* (2013.01); *G01N 11/14* (2013.01); *G01N 2001/2866* (2013.01); *G01N 2203/0092* (2013.01)

(58) Field of Classification Search
None
See application file for complete search history.

(56) References Cited

U.S. PATENT DOCUMENTS 3,597,796 A * 8/1971 Ehrlich .................. G01N 1/286
425/195
5,198,241 A * 3/1993 Marcovecchio ...... B30B 11/005
100/51

(Continued)

FOREIGN PATENT DOCUMENTS

DE 841813 C 6/1952
WO WO-2014/185899 A1 11/2014

OTHER PUBLICATIONS

International Search Report and Written Opinion of the ISA for PCT/GB2016/051332, ISA/EP, Rijswijk, NL, dated Sep. 9, 2016.

*Primary Examiner* — Paul M. West
*Assistant Examiner* — Mark A Shabman
(74) *Attorney, Agent, or Firm* — Harness, Dickey & Pierce, P.L.C.

(57) ABSTRACT

A test apparatus is described comprising a test chamber (12), a powder manipulation device such as a compaction device (20), and a drive arrangement (22) selectively operable to drive the compaction device (20) for axial movement and for rotary movement within or relative to the test chamber (12), the compaction device (20) preferably comprising at least one complete turn of a generally helical screw flight (26). Methods of use of the test apparatus are also described.

15 Claims, 1 Drawing Sheet

(56) References Cited

U.S. PATENT DOCUMENTS

Figure 1:
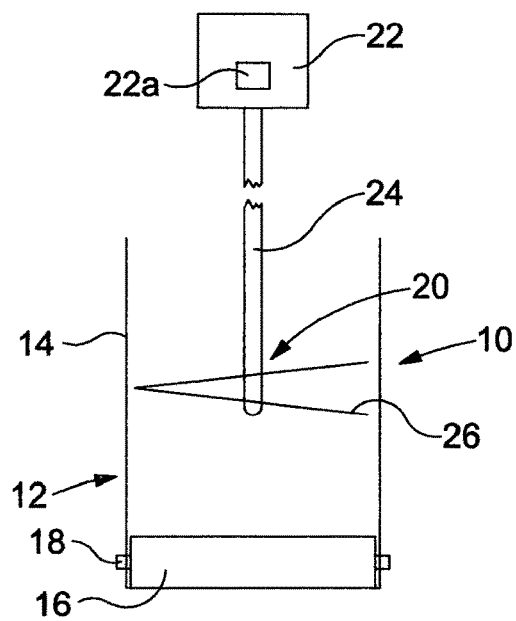

| | | | | |
|---|---|---|---|---|
| 6,481,267 B1 * | 11/2002 | Iles | ............... | G01N 11/14 |
| | | | | 73/54.28 |
| 7,201,040 B2 * | 4/2007 | Bateson | ............... | G01N 11/14 |
| | | | | 73/54.23 |
| 2012/0234102 A1 * | 9/2012 | Johnson | ............... | G01N 3/08 |
| | | | | 73/826 |
| 2013/0086979 A1 * | 4/2013 | Samaniuk | ............... | G01N 11/14 |
| | | | | 73/54.35 |

* cited by examiner

POWDER OR GRANULATED MATERIAL TEST APPARATUS

CROSS-REFERENCE TO RELATED APPLICATIONS

This application is a 371 U.S. National Stage of International Application No. PCT/GB2016/051332, filed May 10, 2016, which claims the benefit of and priority to British Application No. GB1508054.2, filed May 12, 2015. The entire disclosures of the above applications are incorporated herein by reference.

This invention relates to a test apparatus, and in particular to a test apparatus intended for use in deriving data representative of characteristics of a compacted or consolidated powder or granular material. In particular, the invention relates to a test apparatus suitable for use in achieving such compaction or consolidation, and to methods of operation thereof. The test apparatus may further be capable of undertaking tests to provide information relating to characteristics of a material under test.

A number of devices are known for conducting tests on powders or the like. In one such apparatus, a column of the material under test is compacted within a mould or test chamber. The mould or test chamber is then removed, and loads are applied to the compacted material under test to identify how large a load can be applied to the compacted material under test before the column of material yields or fails. Such a test is sometimes referred to as an unconfined yield strength test. It will be appreciated that the accuracy of the data produced by this test will depend, in part, upon the uniformity of the compaction of the test material. If the material is non-uniformly compacted so that regions thereof are compacted to a lesser degree than is desired, then the column of material may yield or fail upon the application of a lower load than would be the case if the material were uniformly compacted to the desired level, and as a result the test results may be erroneous or inaccurate.

Whilst this constitutes one example of a test conducted upon a powder or granular material, other tests are also known, some of which require the powder or granular material under test to be compacted in a controlled fashion as part of or prior to conducting the test. By way of example, powder rheology tests may be conducted upon the compressed powder, for example using the apparatus and methods described in EP0798549B or in WO2003/048743.

Where a compressive load is applied to a quantity of powder or granular material in an attempt to compact the material, the nature of the material can often result in limited radial movement of parts of the material occurring as a result of the application of an axial compacting or compressing load. Where the material is contained within a mould or test chamber, then such movement is limited, but radial stresses will accumulate and the material will be forced against the wall of the mould or test chamber. Frictional resistance between the compacted material and the mould or test chamber can result in parts of the material remote from the surface at which the compressive or compacting load is applied being exposed to a significantly reduced compressive or compacting load. Clearly, as mentioned above, the use of a technique such as this to compact a material for use in a test of the type outlined hereinbefore may lead to inaccuracies in the test results arising from the non-uniform compaction or consolidation of the material being tested.

US2013/0086979 describes an apparatus for use in conducting tests on fluids. The apparatus bears some similarity to the arrangement described above. However, as the characteristics of fluids are very different to those of powder or granulated materials, it will be appreciated that the arrangement of US2013/0086979 is only of very restricted applicability to the present invention. Specifically, US2013/0086979 provides no teaching to suggest that the auger thereof is suitable for use in applying compressive or compacting loads to a powder or granulated material under test.

It is an object of the invention to provide a test apparatus whereby the uniformity of compaction can be enhanced. The invention also relates to methods of conducting a test using the test apparatus.

According to the present invention there is provided a test apparatus comprising a test chamber, a powder manipulation device, and a drive arrangement selectively operable to drive the powder manipulation device for axial movement and for rotary movement relative to the test chamber, the powder manipulation device comprising a generally helical screw flight.

Preferably, the generally helical screw flight is of at least 360° angular extent. It will be appreciated that as a result, movement of the powder manipulation device can achieve controlled compaction of a material under test. The compaction may occur substantially uniformly over the full cross-sectional area of the test chamber.

In use, where the material under test is to be compacted, the material under test is introduced into the test chamber. The powder manipulation device (which will be referred to hereinafter as a compaction device, for convenience) is advanced into the test chamber, being driven for forward rotation whilst being advanced axially into the test chamber. Once the compaction device has reached a predetermined position, rotation thereof may cease. Continued axial movement thereof will serve to compact the material immediately ahead of the compaction device. Subsequently, the compaction device may be retracted by a predetermined distance whilst undergoing reverse rotary motion. After retraction, the compaction process of advancing the compaction device whilst the device is not rotating may be repeated. It will be appreciated that by repeating this process a number of times, the material within the test chamber may be compacted, in stages, with a good degree of uniformity.

In an alternative mode of use, the compaction device may be advanced axially into the material under test, whilst also undergoing forward rotation. Once a predetermined position has been reached, retraction of the compaction device may be undertaken, whilst rotation of the compaction device continues, the speed of retraction of the compaction device being controlled relative to the speed of rotation thereof to ensure that the material is compacted to a desired extent.

The compaction device conveniently comprises a shaft carrying the screw flight. Preferably, a single turn of the generally helical screw flight is provided. However, arrangements in which the screw flight is of greater or lesser angular extent than this, for example including several turns, are possible.

The compaction device is preferably of metallic, for example steel or aluminium construction. Such an arrangement is advantageous in that the compaction device may be of good strength. However, depending upon the application in which the invention is to be used, and the test materials with which it is intended to be used, other materials may be used. By way of example, in some applications the compaction device may be of a suitable plastics material.

The invention also relates to methods of using the test apparatus in conducting tests upon a powder or granular material. In one arrangement, the method comprises the steps of moving the powder manipulation device to a predetermined position, advancing the powder manipulation device whilst holding the device against rotation to compact the material ahead of the powder manipulation device, retracting the powder manipulation device whilst rotating the powder manipulation device to space the screw flight of the powder manipulation device from the compacted material, and repeating the step of advancing the powder manipulation device whilst holding the device against rotation. In this manner, a column of compacted material may be built up, the column having a substantially uniform level of compaction.

In another approach, the powder manipulation device is advanced into the material under test, and is subsequently withdrawn therefrom whilst being rotated, the speed of retraction of the powder manipulation device being controlled relative to the rotary speed thereof to achieve a desired, substantially uniform, level of compaction in the material under test.

In yet another mode of operation, the powder manipulation device may be advanced into the material under test and subsequently withdrawn therefrom whilst held against rotation to remove a quantity of material from the test chamber.

Figure 2:
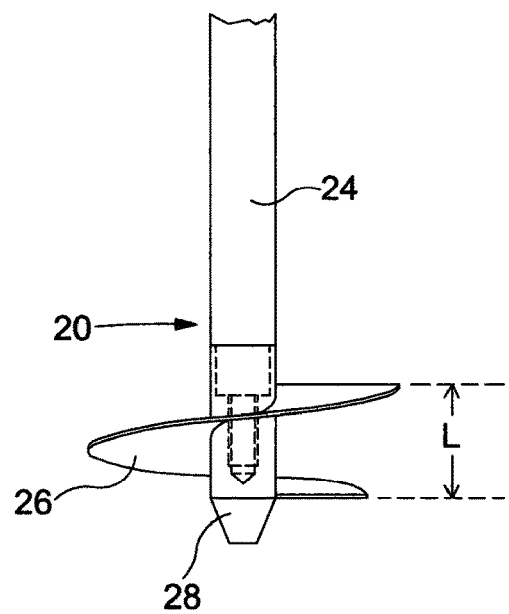

The invention will further be described, by way of example, with reference to the accompanying drawings, in which:

FIG. 1 is a diagrammatic illustration of a test apparatus in accordance with an embodiment of the invention; and FIG. 2 is a view illustrating part of the test apparatus of FIG. 1.

Referring to the accompanying drawings, a test apparatus 10 is illustrated that comprises a test chamber 12, of generally cylindrical form. In the arrangement illustrated, the test chamber 12 takes the form of a hollow tubular member 14 within a lower end of which is located a table 16, a securing mechanism 18 being provided to releasably secure the tubular member 14 to the table 16. The table 16 closes the end of the tubular member 14 and thus defines a container in which materials to be tested can be located, in use. It will be appreciated, however, that this represents merely one design from a wide range of possible designs of test chamber 12.

The apparatus 10 further comprises a powder manipulation device, referred to hereafter, for convenience, as a compaction device 20 capable of being introduced into the test chamber 12, movable axially along the length of the test chamber 12 and also capable of being driven for rotary motion about its axis. A drive mechanism 22 is provided to drive the compaction device 20 for axial movement and for driving the compaction device for rotary movement, the drive mechanism 22 being capable of controlling the speed and direction of both the axial movement and the rotary movement of the compaction device 20. Whilst described and illustrated as having an axially and rotatably moveable compaction device movable relative to a fixed test chamber, it will be appreciated that the compaction device could be fixed and the test chamber movable. Indeed, one of the compaction device and the test chamber could be rotatable and the other axially movable, if desired.

As best shown in FIG. 2, the compaction device 20 comprises an elongate shaft 24 connected, at one end, to the drive mechanism 22, and carrying at the other end thereof a single turn of a generally helical screw flight 26. Conveniently, the compaction device 20 is of metallic construction, for example of steel or aluminium form, and as a result is capable of being used in applying significant compacting loads to the material under test, in use, and being relatively resistant to wear. It will be appreciated, however, that depending upon the application in which the invention is to be employed, other materials may be used. By way of example, in some arrangements suitable plastics materials may be used.

The screw flight 26 is conveniently formed on the outer surface of a cylindrical stub 28 which is secured to the end of the shaft 24. By way of example, the stub 28 and shaft 24 may be coupled to one another by interengaging screw thread formations. However, other techniques such as welding may be employed. Alternatively, the flight 26 may be formed directly upon the shaft 24 with no stub 28 being present.

The outer diameter of the flight 26 is preferably slightly smaller than the inner diameter of the test chamber 12. By way of example, a clearance of the order of 1-2 mm may be present therebetween, to minimise the risk of contact and wear therebetween, in use. However, the clearance therebetween may be greater or smaller than this without departing from the scope of the invention.

As shown in FIG. 2, the single turn of the flight 26 has an axial pitch length L. The value of the pitch length L may be selected depending upon the application in which the invention is to be used and for simplicity of manufacture. In the arrangement illustrated, the pitch length L is approximately 16 mm, but it will be understood that the invention is not restricted in this regard.

The test arrangement 10 may be used in a number of ways to achieve compaction of a material under test located within the test chamber 12. By way of example, in one mode of operation, the material under test is introduced into the test chamber 12. The compaction device 20 is then introduced into the test chamber 12 under the control of the drive arrangement 22. The compaction device 20 is conveniently advanced axially into the test chamber 12 whilst being rotated in the forward direction, the speed of rotation of the compaction device 20 being such that it rotates through a single revolution during the time taken for the compaction device 20 to be advanced by an axial distance equal to the pitch length L. By advancing the compaction device 20 at this speed, it will be appreciated that the compaction device 20 applies only a minimal compacting load to the material under test, the flight 26 of the compaction device 20 effectively being 'screwed into' the material under test.

The compaction device 20 continues to be advanced into the material under test in this fashion until the leading edge of the flight 26 of the compaction device 20 approaches the table 16, being spaced therefrom by a predetermined distance of, say, in the region of 10 mm. Depending upon the design of the compaction device, the tip of the compaction device may be closer to the table 16 than this. It will be appreciated that once this position is reached, there will be approximately 10 mm of uncompacted material immediately ahead of the flight of the compaction device 20. Once this position is reached, rotation of the compaction device 20 is interrupted, the drive mechanism 22 holding the compaction device 20 in a fixed angular position, resisting rotation thereof. With the compaction device 20 held against rotary or angular movement, the drive mechanism applies a load to the compaction device 20 urging the compaction device 20 to advance axially. It will be appreciated that the axial movement of the compaction device 20, whilst the device 20 is held against rotation, results in the compaction device 20 compressing the material immediately ahead thereof, compacting or consolidating the material.

As the flight 26 extends around at least one complete turn, it will be appreciated that the material under test located over substantially the entire cross section of the chamber 12 is subject to the application of a compressive, compacting load, the compacting load being applied substantially uniformly over the full cross-sectional area.

The drive mechanism 22 conveniently incorporates a sensor 22a operable to measure the resistance to advancing movement of the compaction device. By way of example, a load cell or the like may be used as the sensor 22a. However, it will be appreciated that the invention is not restricted in this regard. By using the output of the sensor 22a in controlling the movement of the compaction device 20, it will be appreciated that the compaction or consolidation of the material to a desired level can be accurately achieved, the axial movement of the compaction device 20 ceasing when a predetermined resistance to axial movement of the compaction device 20 in the compaction direction is sensed, indicating that a desired level of compaction or consolidation has been achieved.

After compaction of the material ahead of the compaction device 20 in this manner, the compaction device 20 is retracted by a predetermined distance, for example by 10 mm, whilst being rotated in the reverse direction at substantially the speed mentioned hereinbefore such that during the retraction of the compaction device 20, substantially no compacting or separating load is applied to the material under test. After retraction in this manner, it will be appreciated that there will be a layer of uncompacted material between the compaction device 20 and the previously compacted layer of material, the thickness of the uncompacted layer of material substantially equating to the axial distance through which the compaction device 20 has been retracted. The compaction device 20 is then held against rotation whilst being driven in the forward direction to compact the aforementioned uncompacted layer of material in the manner set out above.

The process described above may be repeated a number of times to form a column of material of a desired height or length that is substantially uniformly compacted, the degree of compaction or consolidation being accurately controlled.

Once compacted, a range of tests may be conducted upon the material. By way of example, the material may be removed from the test chamber, and an unconfined yield strength test conducted upon the material. Alternatively, with the material contained within the test chamber, powder rheology tests may be conducted upon the compressed powder, for example using the apparatus and methods described in EP0798549B. It will be appreciated that the precise nature of the tests conducted upon the compressed material do not form part of the present invention and so are not described herein in further detail.

Whilst the description hereinbefore describes one method of use of the test apparatus of this embodiment of the invention, it will be appreciated that the apparatus may be used in other operating modes. By way of example, whilst in the arrangement hereinbefore the compaction of the material is achieved in a series of compaction steps, the arrangement of this embodiment of the invention may alternatively be operated to apply a substantially continuous compacting or loosening load to the material to aid the formation of a compacted or loosened column of material of a substantially uniform level of compaction. In order to operate the test apparatus in this manner, a quantity of powder to be compacted is introduced into the test chamber 12, and the compaction device 20 is introduced into the material and driven to the end of the test chamber 12 closed by the table 16 in substantially the manner outlined hereinbefore, rotating the compaction device in the forward direction to 'screw' it into the material whilst the compaction device is moved axially towards the table 16. Once the compaction device 20 has reached this position, retraction of the compaction device 20 commences. During retraction, the compaction device 20 is rotated in the reverse direction at a rotary speed faster than that at which it was introduced so that rather than being merely 'screwed out' of the material causing minimal axial displacement thereof, the rotation of the compaction device 20 drives material past the screw flight 26 substantially in the manner of an auger, and so causes the material immediately beneath the flight 26 thereof to be compacted as the compaction device 20 is withdrawn. The speed of retraction relative to the speed of rotation of the compaction device 20 controls the degree of compaction that occurs. It will be appreciated that this technique allows a greater degree of uniformity of compaction to be attained. As with the arrangement described hereinbefore, the output of a sensor, in this case sensitive to, for example, the resistance to rotation of the compaction device 20, and so providing an indication of the degree of compaction that has been achieved, may be used in controlling the speeds of rotation and retraction of the compaction device 20 to ensure that the desired level of compaction or consolidation of the material is achieved. By way of example, where the sensor 22a is sensitive to the shear stress, the rotational speed of the compaction device 20 may be set at a fixed rate and the upwards axial movement of the compaction device 20 adjusted to ensure the sensed shear stress (or torque) lies within a predetermined range. If the detected shear stress is too high, then the rate at which the compaction device 20 is lifted will be increased to bring the detected shear stress to an acceptable, and vice versa. Of course, alternatively, the axial movement could be controlled in such a fashion that it occurs at a substantially uniform rate whilst the speed of rotary movement is varied to achieve the desired level of compaction.

It will be appreciated from the above description that the apparatus described hereinbefore may be used in a number of ways to achieve compaction or loosening of the material under test in a controlled manner. When the compaction device 20 is being introduced into the material under test or withdrawn therefrom, by controlling the speed of rotation of the compaction device 20 relative to the axial speed of movement thereof, the effective 'angle of attack' of the flight 26 can be varied despite the flight 26 itself being a rigid structure on the shaft 24 to achieve consolidation of the material or lifting and loosening thereof. By way of example, if the compaction device 20 is rotated whilst being moved downwards, the speed of axial movement relative to that of rotary movement being such that the effective angle of attack is steeper than the actual helix angle of the flight 26, then some compaction will occur during the downwards movement. Similarly, if it raised a steeper angle of attack than the helix angle of the flight 26, then lifting and loosening of the material will occur.

As mentioned above, the consolidation or loosening can be used to prepare the material for subsequent tests, for example of the type referred to hereinbefore.

In the arrangements described hereinbefore, the compaction device 20 is used to consolidate or loosen substantially the full cross sectional area of the material located within the test chamber. It will be appreciated that this need not always be the case. If desired, the outer diameter of the flight 26 could be considerably smaller than the internal diameter of the test chamber 12, for example around half the diameter thereof. With such an arrangement, in one mode of operation the compaction device 20 could be rotated in the forward direction whilst being axially driven towards the table 16. Once located at a desired depth, which may be adjacent the table 16, rotation of the compaction device 20 may cease and the compaction device 20 withdrawn axially to shear a central column of material from the test material located within the test chamber, leaving an annular column of material in position upon which tests can be conducted. Conveniently, where the compaction device 20 is to be used in this manner, the flight 26 of the compaction device 20 is of multi-turn form, extending over substantially the full height of the material in the test chamber 12.

Whilst one embodiment of a test apparatus 10 in accordance with the invention, and a couple of methods of use thereof, are set out hereinbefore, it will be appreciated that a wide range of modifications and alterations may be made, both to the test apparatus itself and to the methods of use thereof, without departing from the scope of the invention as defined by the appended claims.

The invention claimed is:

1. A powder or granulated material compaction apparatus comprising a test chamber, a manipulation device, and a drive arrangement selectively operable to drive the manipulation device independently for axial movement and for rotary movement relative to the test chamber, the manipulation device comprising a generally helical screw flight so that the selective axial and/or rotary movement of the manipulation device, in use, serves to compact a powder or granulated material located within the test chamber by applying a compacting load thereto, the compacting load being applied substantially uniformly over substantially the entire cross section of the test chamber.

2. The apparatus according to claim 1, wherein the manipulation device comprises a shaft carrying the flight.

3. The apparatus according to claim 1, wherein the generally helical screw flight is of 360° angular extent.

4. The apparatus according to claim 1, wherein the manipulation device is of metallic construction.

5. The apparatus according to claim 1, further comprising a sensor sensitive to the resistance to axial movement of the manipulation device.

6. The apparatus according to claim 1, further comprising a sensor sensitive to the resistance to rotary movement of the manipulation device.

7. The apparatus according to claim 1 and adapted for use in conducting unconfined yield strength tests.

8. The apparatus according to claim 1 and adapted for use in conducting powder rheology tests.

9. A method of using a powder or granulated material compaction apparatus comprising a test chamber, a manipulation device, and a drive arrangement selectively operable to drive the manipulation device independently for axial movement and for rotary movement relative to the test chamber, the manipulation device comprising a generally helical screw flight so that the selective axial and/or rotary movement of the manipulation device, in use, serves to compact a powder or granulated material located within the test chamber by applying a compacting load thereto, the compacting load being applied substantially uniformly over substantially the entire cross section of the test chamber, the method comprising the steps of:
   moving the manipulation device to a predetermined position relative to the chamber;
   advancing the manipulation device relative to the chamber whilst holding the manipulation device against rotation relative to the chamber to compact the material ahead of the manipulation device;
   retracting the manipulation device relative to the chamber whilst rotating the manipulation device relative to the chamber to space the flight of the manipulation device from the compacted material;
   and repeating the step of advancing the manipulation device relative to the chamber whilst holding the device against rotation relative to the chamber.

10. The method as claimed in claim 9, wherein during the retracting step the manipulation device is retracted at a speed such that it is retracted by a distance substantially equal to a pitch length of the flight per revolution of the manipulation device.

11. The method as claimed in claim 9, wherein during the advancing step a resistance to movement of the manipulation device is monitored.

12. A method of using a powder or granulated material compaction apparatus comprising a test chamber, a manipulation device, and a drive arrangement selectively operable to drive the manipulation device independently for axial movement and for rotary movement relative to the test chamber, the manipulation device comprising a generally helical screw flight so that the selective axial and/or rotary movement of the manipulation device, in use, serves to compact a powder or granulated material located within the test chamber by applying a compacting load thereto, the compacting load being applied substantially uniformly over substantially the entire cross section of the test chamber, the method comprising the steps of:
   advancing the manipulation device into the material under test; and
   subsequently withdrawing the manipulation device from the material whilst rotating the manipulation device relative to the material, the speed of retraction of the manipulation device being controlled relative to the rotary speed thereof to achieve a desired level of compaction in the material under test.

13. The method according to claim 12, wherein during the withdrawal step the manipulation device is retracted at a speed such that it is retracted by a distance greater than a pitch length of the flight per revolution of the manipulation device.

14. The method according to claim 12, wherein during the withdrawal step a resistance to rotation of the manipulation device is monitored.

15. A method of using a powder or granulated material compaction apparatus comprising a test chamber, a manipulation device, and a drive arrangement selectively operable to drive the manipulation device independently for axial movement and for rotary movement relative to the test chamber, the manipulation device comprising a generally helical screw flight so that the selective axial and/or rotary movement of the manipulation device, in use, serves to compact a powder or granulated material located within the test chamber by applying a compacting load thereto, the compacting load being applied substantially uniformly over substantially the entire cross section of the test chamber, the method comprising the steps of:
   advancing the manipulation device into the material under test whilst rotating the manipulation device; and subsequently withdrawing the manipulation device therefrom whilst holding the manipulation device against rotation to remove a quantity of material from the chamber.

* * * * *